United States Patent [19]
Alkhazov et al.

[11] Patent Number: 4,519,992
[45] Date of Patent: May 28, 1985

[54] PROCESS FOR PURIFYING GASES FROM HYDROGEN SULPHIDE

[76] Inventors: Tofik G. O. Alkhazov, prospekt Kirova, 40, kv. 39, Baku; Jury P. Korotaev, prospekt Lenina, 69, korpus 2, Moscow; Albert A. Vartanov, ulitsa Michurina, 39, blok 4, kv. 25, Baku, all of U.S.S.R.

[21] Appl. No.: 613,892

[22] Filed: May 24, 1984

[30] Foreign Application Priority Data

May 26, 1983 [SU] U.S.S.R. ............... 3591260

[51] Int. Cl.$^3$ ............................................. B01D 53/36
[52] U.S. Cl. ..................... 423/230; 423/231; 423/573 G
[58] Field of Search ........... 423/224, 230, 231, 573 G, 423/573 R

[56] References Cited

U.S. PATENT DOCUMENTS

| 3,781,445 | 12/1973 | Moss et al. | 423/574 |
|---|---|---|---|
| 4,088,736 | 5/1978 | Courty et al. | 423/230 |
| 4,233,276 | 11/1980 | D'Souza et al. | 423/230 |
| 4,313,820 | 2/1982 | Farha, Jr. et al. | 423/230 X |
| 4,363,790 | 12/1982 | Anderson et al. | 423/230 |
| 4,399,112 | 8/1983 | Voirin | 423/230 |
| 4,427,576 | 1/1984 | Dupin | 423/224 X |

FOREIGN PATENT DOCUMENTS

| 78690 | 5/1983 | European Pat. Off. | 423/573 G |
|---|---|---|---|
| 856974 | 8/1981 | U.S.S.R. | 423/573 G |

Primary Examiner—Earl C. Thomas
Attorney, Agent, or Firm—Burgess, Ryan & Wayne

[57] ABSTRACT

A process for purifying gases from hydrogen sulphide which comprises oxidation of hydrogen sulphide with air oxygen at a volume ratio between hydrogen sulphide to oxygen equal to 1:1–1.5 on a catalyst having the following composition, % by weight: titanium dioxide—10-30, iron oxide—20-30, zinc oxide—20-25, chromium oxide—20-50. The process is conducted at a temperature within the range of from 220° to 260° C. and at a space velocity of the gas mixture of from 3,000 to 15,000 hr$^{-1}$.

1 Claim, No Drawings

PROCESS FOR PURIFYING GASES FROM HYDROGEN SULPHIDE

FIELD OF THE INVENTION

The present invention relates to the art of purification of gases from sulphurous compounds and, more specifically, it relates to a process for purification of gases from hydrogen sulphide and is useful in the gas and petroleum-refining industries.

BACKGROUND OF THE INVENTION

Natural gas or gases resulting from petroleum refining prior to their processing are subjected to a preliminary purification from sulphurous compounds, in particular, hydrogen sulphide.

One of the prior art processes for purification of gases from hydrogen sulphide comprises its chemical interaction with solid reactants (cf. B.S. Al'tschuler, A.A.Gavrilova "High-Temperature Purification of Gases from Sulphurous Compounds", 1969, "Nauka" Publishers, Moscow, p. 51–101). This process enables fine purification of the gas, substantially 100% recovery of hydrogen sulphide, but its implementation necessitates application of high temperatures and is accompanied by the formation of large quantities of $SO_2$ as a result of interaction of oxygen with sulphides upon regeneration of the absorbents.

Known in the art is a process for purification of a gas from hydrogen sulphide by way of oxidation thereof on a catalyst-activated carbon (cf. Journal of Catalysis, v.35, No. 1, 1974; M.Stejns, P.Mars "The Role of Sulfur Trapped in Micropores in the Catalytic Partial Oxidation of Hydrogen Sulfide with Oxygen, p. 11–17).

The process is effectively performed within a broad temperature range of from 20° to 250° C. However, at temperatures of up to 200° C. the resulting sulphur is cooled on the catalyst, deactivates it so that the efficiency of purification is considerably lowered. At a temperature above 200° C. sulphur is oxidized into $SO_2$, wherefore the process selectivity is impaired.

It is known to purify gas from hydrogen sulphide with the use of zeolite catalysts (Proceedings of Moscow Mendeleev Technological Chemical Institute, issue 56, 1967; M.A.Adlivankina, N.V.Kel'tsev, N.S.Torocheshnikov, Yu.I.Schumyatsky "A Study on the Process of Partial Oxidation of Hydrogen Sulphide on Zeolities", pp. 160–164). The process is conducted at low space velocities (890 $hr^{-1}$) and elevated temperatures (324° C.). But even under these conditions no complete recovery of hydrogen sulphide from gases is achieved.

Known is a process for purification of gases from hydrogen sulphide on a catalyst comprising bauxite (Gazovaya Promyshlennost/Gas Industry/, No. 8, August 1966; Yu.N.Brodsky, V.I.Gerus, S.M.Goland, Ya.I.Frenkel "Production of Sulphur at the Pokhvistnevskaya Gas Compressor Station", pp. 42–44). The maximum degree of gas purification in carrying out the process as taught by this reference does not exceed 93% even at the low space velocity of 300 $hr^{-1}$ and at the temperature of 280° C. To achieve a 96% degree of conversion of hydrogen sulphide, it is necessary to carry out the process in two stages with separation of water at the intermediate stage to prevent deactivation of bauxite, since an increase in the concentration of water vapours from 0.9 to 12.9% lowers the degree of the gas purification after the first step from 85% to 42% (cf. U.S. Pat. No. 3,781,445 issued Dec. 25, 1973).

The gas purification from hydrogen sulphide by this process with the use of alumina does not provide for a high selectivity of the process. Thus, at the temperature of 235° C. and space velocity of 3,000 $hr^{-1}$ nearly 20% of hydrogen sulphide are converted into sulphurous anhydride (Newsletters of Higher School, "petroleum and Gas", No. 2, February 1979; T.G.Alkhazov, A.A.-Vartanov "On Catalytic Oxidation of Natural Gas Hydrogen Sulphide", p. 41–44).

Carrying out the process with the use of iron-oxide catalyst does not provide high process characteristics within a wide range of space rates and temperatures either. At the space velocity of 15,000 $hr^{-1}$ and at the temperature of 300° C. the degree of the gas purification is not more than 95%. Decreasing the space velocity contributes to a lesser selectivity of the process (cf. USSR Inventor's Certificate No. 865777, Cl. C01 B 17/04, 1981).

Also known in the art is a process for oxidation of hydrogen sulphide to elemental sulphur on a catalyst containing oxides of titanium and iron with the following content of the components, % by weight: iron oxide 0.05–0.3, titanium dioxide—the balance (cf. USSR Inventor's Certificate No. 856974, Cl. C 01 B 17/04, 1981). The maximum conversion of hydrogen sulphide into sulphur equal to 99.5% with the 100% selectivity is attained at space velocities of 2,500 to 3,000 $hr^{-1}$ and temperatures within the range of from 285° to 300° C. This process makes it possible to purify gases with a high content of hydrogen sulphide of up to 25% by volume. A high conversion and selectivity can be attained only in carrying out the process in two stages with an obligatory intermediate trapping of sulphur and water and with separate supply of oxygen to each stage. A strictly predetermined ratio of $O_2$ to $H_2S$ should be maintained at each stage, this involving certain difficulties in the process control. Furthermore, as it has been already mentioned hereinbefore, a 100% conversion of hydrogen sulphide and a 99.5% selectivity of its oxidation into elemental sulphur are ensured at low space velocities of up to 3,000 $hr^{-1}$ and at elevated temperatures of up to 300° C.

OBJECT OF THE INVENTION

It is an object of the present invention to provide such a process for purification of gases from hydrogen sulphide which would make it possible to simplify the process control and improve its efficiency.

SUMMARY OF THE INVENTION

This object is accomplished by the provision of a process for purification of gases from hydrogen sulphide by way of oxidation thereof with oxygen at a volume ratio of hydrogen sulphide to oxygen equal to 1:1–1.5 on a catalyst containing the following components, percent by weight: titanium dioxide—10–30, iron oxide—20–30, zinc oxide—20–25, chromium oxide—20–50, at a temperature of 220° to 260° C. and at a space velocity of passing the gas mixture of from 3,000 to 15,000 $hr^{-1}$.

The process according to the present invention makes it possible to achieve a high degree of purification from hydrogen sulphide of not less than 98% with a selectivity of not less than 98%. The process is highly efficient, since it is performed in a single stage and proceeds at high space velocities of up to 15,000 $hr^{-1}$.

An important advantage of the process according to the present invention is irreversibility of the process ensuring a quantitative conversion of hydrogen sulphide into elemental sulphur without the formation of a by-product, i.e. sulphurous anhydride.

DETAILED DESCRIPTION OF THE INVENTION

The starting gas, e.g. natural gas or gas resulting from petroleum refining is mixed with air so that the volume ratio of oxygen to hydrogen sulphide in the gas mixture be equal to 1-1.5:1. The resulting gas mixture is passed onto a catalyst containing the following components, percent by weight: titanium dioxide—10-30, iron oxide—20-30, zinc oxide—20-25, chromium oxide—20-50. The oxidation process is conducted in one stage at a temperature within the range of from 220° to 260° C. and at a space velocity of the gas mixture of 3,000 to 15,000 hr$^{-1}$. Under the above-specified conditions hydrogen sulphide is oxidized and quantitatively converted into sulphur.

The process according to the present invention makes it possible to obtain in a single stage practically a 100% conversion of hydrogen sulphide into sulphur without the formation of sulphurous anhydride.

For a better understanding of the present invention some specific examples are given hereinbelow by way of illustration.

EXAMPLE 1

Subjected to purification is a hydrocarbon gas containing 3 vol.% of hydrogen sulphide. This gas is mixed with air so that the volume ratio of hydrogen sulphide to oxygen be equal to 1:1.5 and then fed onto a catalyst having the following composition, % by weight: $Fe_2O_3$—25, $TiO_2$—25, ZnO—25. The process is conducted at the temperature of 240° C. and at the space velocity of 3,000 hr$^{-1}$. As a result, the degree of purification of the gas from hydrogen sulphide is equal to 100%, the process selectivity is 98.8%.

To prepare the catalyst, in separate vessels there are dissolved: 25.5 g of iron chloride in 943 ml of distilled water, 26.3 g of chromium chloride in 1,000 ml of water, 12.5 of zinc chloride in 916 ml of water and 17.8 g of titanium chloride in 940 ml of water. To the thus-prepared solutions a 3N aqueous solution of ammonia is added to ensure complete precipitation of hydroxides of iron, chromium, zinc and titanium. The hydroxides are poured into one vessel, thoroughly intermixed and the mixture is washed with distilled water till a negative reaction for chloride ions is observed. Then the catalyst is filtered off, moulded, air-dried at room temperature and calcined at the temperature of 500° C. for 4 hours. As a result, a catalyst of the above-specified composition is obtained. The catalysts in the subsequent Examples are prepared following a similar procedure.

EXAMPLE 2

A hydrocarbon gas containing 3% by volume of hydrogen sulphide is subjected to purification. This gas is mixed with air so that the volume ratio of hydrogen sulphide to oxygen is equal to 1:1.5 and fed onto a catalyst having composition specified in Example 1 hereinabove. The process is conducted at the temperature of 220° C. and the space velocity of 9,000 hr$^{-1}$. As a result, the degree of purification of the gas from hydrogen sulphide is 99.6%, the process selectivity is 100%.

EXAMPLE 3

A hydrocarbon gas containing 3% by volume of hydrogen sulphide is subjected to purification. This gas is mixed with air so that the volume ratio of hydrogen sulphide to oxygen is equal to 1:1 and then fed onto a catalyst with the composition specified in Example 1. The process is conducted at the temperature of 260° C. and the space velocity of 15,000 hr$^{-1}$. As a result, the degree of purification of the gas from hydrogen sulphide is 99.9%, the process selectivity is 100%.

EXAMPLE 4

A hydrocarbon gas containing 3% by volume of hydrogen sulphide is subjected to purification. This gas is mixed with air so that the volume ratio of hydrogen sulphide to oxygen is equal to 1:1.5 and fed onto a catalyst having the following composition, % by weight: $Fe_2O_3$—20, $Cr_2O_3$—50, $TiO_2$—10, ZnO—20. The process is conducted at the temperature of 240° C. and the space velocity of 15,000 hr$^{-1}$. As a result, the degree of the gas purification from hydrogen sulphide is 98.6%, the process selectivity is 100%.

EXAMPLE 5

A gas containing 3 vol. % of hydrogen sulphide is subjected to purification. This gas is mixed with air so that the volume ratio of hydrogen sulphide to oxygen be equal to 1:1 and fed onto a catalyst having the following composition, % by weight: $Fe_2O_3$—30, $Cr_2O_3$—20, $TiO_2$—30, ZnO—20. The process is conducted at the temperature of 240° C. and the space velocity of 15,000 hr$^{-1}$. As a result, the degree of the gas purification from hydrogen sulphide is 99.1% the process selectivity is 100%.

Examples 6, 7 and 8 are presented in a tabulated form. A gas containing 3% by volume of hydrogen sulphide is subjected to purification. This gas is mixed with air so that the volume ratio of hydrogen sulphide to oxygen is equal to 1:1 and fed onto a catalyst the composition specified in the Table hereinbelow. The process is conducted at a temperature within the range of from 220° to 260° C. and the space velocity of 6,000 hr$^{-1}$. The process parameters are shown in the following Table.

TABLE

| | | | | | Degree of gas purification from H$_2$S ($\alpha$) and selectivity of the process. (S) %. at temperatures, °C. | | | | | |
|---|---|---|---|---|---|---|---|---|---|---|
| Example | Catalyst composition, % by weight | | | | 220 | | 240 | | 260 | |
| No. | Fe$_2$O$_3$ | Cr$_2$O$_3$ | TiO$_2$ | ZnO | $\alpha$ | S | $\alpha$ | S | $\alpha$ | S |
| 1 | 2 | 3 | 4 | 5 | 6 | 7 | 8 | 9 | 10 | 11 |
| 6 | 20 | 50 | 10 | 20 | 98.5 | 100 | 99.6 | 100 | 99.8 | 98.6 |
| 7 | 25 | 25 | 25 | 25 | 100 | 100 | 100 | 100 | 100 | 99.9 |
| 8 | 30 | 20 | 30 | 20 | 100 | 100 | 100 | 100 | 100 | 97.8 |

What is claimed is:

1. A process for purifying gases from hydrogen sulphide, comprising oxidizing of hydrogen sulphide with oxygen at a volume ratio of hydrogen sulphide to oxygen of 1:1-1.5 on a catalyst containing, % by weight: titanium dioxide—10-30, iron oxide—20-30, zinc oxide—20-25, chromium oxide—20-50 at a temperature ranging from 220° to 260° C. and at a space velocity of the gas mixture of 3,000 to 15,000 $hr^{-1}$.

* * * * *